United States Patent [19]
Larson et al.

[11] Patent Number: 5,444,242
[45] Date of Patent: Aug. 22, 1995

[54] SCANNING AND HIGH RESOLUTION ELECTRON SPECTROSCOPY AND IMAGING

[75] Inventors: Paul E. Larson, Bloomington; Paul W. Palmberg, Edina, both of Minn.

[73] Assignee: Physical Electronics Inc., Eden Prairie, Minn.

[21] Appl. No.: 201,912

[22] Filed: Feb. 25, 1994

Related U.S. Application Data

[63] Continuation-in-part of Ser. No. 953,429, Sep. 29, 1992, Pat. No. 5,315,113.

[51] Int. Cl.$^6$ .......................................... H01J 49/48
[52] U.S. Cl. .................................. 250/305; 250/306
[58] Field of Search ............... 250/305, 306, 302, 310, 250/251; 378/84, 85

[56] References Cited

U.S. PATENT DOCUMENTS

| | | | |
|---|---|---|---|
| Re. 33,275 | 2/1990 | Wardell et al. | 250/305 |
| 3,567,926 | 3/1971 | Siegbahn | 250/49.3 |
| 3,617,741 | 11/1971 | Siegbahn et al. | 250/49.5 |
| 3,766,381 | 10/1973 | Watson | 250/49.5 |
| 3,772,522 | 11/1973 | Hammond et al. | 250/503 |
| 3,787,692 | 1/1974 | Anderson | 250/305 |
| 4,048,498 | 9/1977 | Gerlach et al. | 250/305 |
| 4,358,680 | 11/1982 | Read | 250/305 |
| 4,680,467 | 7/1987 | Bryson, III et al. | 250/305 |
| 4,752,685 | 6/1988 | Shiokawa et al. | 250/305 |
| 4,764,673 | 8/1988 | Bryson et al. | 250/305 |
| 4,810,879 | 3/1989 | Walker | 250/305 |
| 4,810,880 | 3/1989 | Gerlach | 250/305 |
| 5,118,941 | 6/1992 | Larson | 250/310 |
| 5,127,028 | 6/1992 | Wittry | 378/84 |

OTHER PUBLICATIONS

"Computer Optimization Of Retarding Lens Sustems For ESCA Spectrometers" by B. Wannberg and A. Skollermo. Journal of Electron Spectroscopy and Related Phenomena, 10, 44–78 (1977).

"A Wide-angle Secondary Ion Probe for Organic Ion Imaging" by C. C. Grimm, R. T. Short, and P. J. Todd, J. AM. Soc. Mass. Spectrum 1991, 2, 362–371.

"AXIS: An Imaging X-Ray Photoelectron Spectrometer" by I. W. Drummond, F. J. Street, L. P. Ogden, and D. J. Surman, Scanning 13, 149–163 (Mar.–Apr. 1991).

Primary Examiner—Paul M. Dzierzynski
Assistant Examiner—Kiet T. Nguyen
Attorney, Agent, or Firm—H. S. Ingham

[57] ABSTRACT

An instrument for surface analysis includes rastering an electron beam across an anode to generate x-rays. A concave Bragg monochromator focuses an energy peak of the x-rays to a specimen surface, the x-rays rastering the surface to emit photoelectrons. An analyzer provides information on the photoelectrons and thereby chemical species in the surface. A second detector of low energy photoelectrons is cooperative with the rastering to produce a scanning photoelectron image of the surface for imaging of the specimen. Alternatively a lens formed of two concave grids transits the photoelectrons to the analyzer with selectively modified energy so that the analyzer detects either higher energy electrons characteristic of chemical species or lower electrons for the image. The monochromator is formed of platelets cut from an array of platelets in a single crystal member. For imaging of insulating specimens, the surface is flooded periodically with electrons, and the signals are omitted from the image during the flooding. For chemometric information summed over the surface of insulators, data from the edges is omitted from the summing.

24 Claims, 5 Drawing Sheets

SCANNING AND HIGH RESOLUTION ELECTRON SPECTROSCOPY AND IMAGING

This application is a continuation-in-part of U.S. patent application Ser. No. 953,429, filed Sep. 29, 1992, now U.S. Pat. No. 5,315,113.

This invention relates generally to electron microanalysis and imaging of surfaces, and particularly to high-resolution x-ray scanning photoelectron spectroscopy and imaging, and to an electron lens system for adapting electron energy analyzers for imaging in electron spectrometric instruments.

BACKGROUND OF THE INVENTION

A variety of electron microscopes and associated surface analyzers have evolved in recent years. One approach to chemometric surface analysis is electron spectroscopy for chemical analysis (ESCA) which involves irradiating a sample surface with ultraviolet or preferably x-rays and detecting the characteristic photoelectrons emitted. The latter method is also known as x-ray photoelectron spectroscopy (XPS). The photoelectrons are filtered by an electrostatic or magnetic analyzer which allow only electrons of a specified narrow energy band to pass through to a detector. The intensity of the detected beam typically represents the concentration of a given chemical constituent on or near a specimen surface. U.S. Pat. No. 3,766,381 (Watson) describes such a system.

Electron kinetic energies are detected or analyzed by magnetic or electrostatic devices that deflect charged particles according to their velocities. Electrostatic types include coaxial cylindrical, radial cylindrical and radial hemispherical. The Gerlach et al patent discloses the coaxial cylindrical analyzer. A radial cylindrical analyzer is taught in U.S. Pat. No. 4,764,673 (Bryson et al). The Watson patent and U.S. Pat. No. 4,358,680 (Read) describe the electrostatic hemispherical type of analyzer. Radial analyzers (cylindrical and hemispherical) generally are preceded by a lens system formed of rings, cylinders and/or grids for adjusting electron energy and focusing the electrons into the analyzer. Such lenses are disclosed in the aforementioned U.S. Pat. Nos. 4,358,680 and 4,764,673. The design of such lenses that vary retardation over a moderate range of retardation ratios is described in an article "Computer Optimization of Retarding Lens Systems for ESCA Spectrometers" by B. Wannberg and A. Sköllermo, J. Electron Spectroscopy and Related Phenomena, 10 45–78 (1977). These systems are directed to area analyses using a relatively low solid angle of electron collection, and a wider range of ratios is desirable.

Another method for analyzing surfaces utilizes secondary Auger electrons generated at a small area of sample surface by a focused primary electron beam. Surface mapping of elements is accomplished by scanning with the primary electron beam. An example of a scanning Auger-microprobe utilizing a coaxial cylindrical type of electrostatic electron analyzer is provided in U.S. Pat. No. 4,048,498 (Gerlach et al).

A more commonly known instrument is a scanning electron microscope (SEM) in which a focused electron beam is rastered over a specimen surface. Secondary electrons emitted from the surface are detected in correlation with rastering positions. The secondary electron signals are processed electronically to provide a picture or image of topographical features of the surface. An SEM itself does not provide chemometric analysis, although x-ray emissions induced by the incident electrons are used for such analysis. Another limitation of the SEM is imaging the surface of electrical insulators, because of rapid charge buildup from the incident beam of electrons. Conductive coatings or other techniques are used to alleviate charging, but at the loss of surface details, time and cost of extra preparation, and loss of ability to remove surface layers during analysis. U.S. Pat. No. 5,118,941 (Larson), of the present assignee, discloses that insulator specimens can be imaged with a single frame of SEM rastering, but at the expense of resolution.

Separate detectors generally are used for the analyzing and imaging functions in the same instrument, for example as further disclosed in the Larson patent. This adds cost and employs space which could otherwise be available for other purposes. Also, particularly for low current systems, there is a need for detection of a greater proportion of electrons from the sample for imaging, and for rejecting background from stray electrons, ions and excited neutrals which originate from other sources. For energy analyzers the sample generally is kept field-free, whereas for imaging, a field is applied so as to maximize the quantity of electrons collected by the detector.

The Larson patent also discloses a system for locating target area for microanalysis of a specimen surface, using an SEM in conjunction with the microanalyzer. Backscattered electrons from the SEM electron beam are passed through the analyzer for producing a further image that is superimposed on the SEM image, such that the further image represents the target area for microanalysis.

Thus systems involving electron beam impingement on a specimen surface have evolved into high sensitivity instruments, in which very small areas may be selected for analysis. Rastering can be used to provide images or chemical mapping of the surface.

However, similar small-area sensitivity and raster mapping has been elusive for x-ray photoelectron spectroscopy (XPS).

X-rays from an anode target have been focused onto the specimen by means of a concave crystal monochrometer, as taught in U.S. Pat. Nos. 3,567,926 (Siegbahn), 3,617,741 (Siegbahn et al), 4,680,467 (Bryson et al), 4,752,685 (Shiokawa et al) and 5,127,028 (Wittry). A method of construction of a concave monochrometer for focusing x-rays is disclosed in U.S. Pat. No. 3,772,522 (Hammond et al), in which a quartz crystal disk is brazed with a metal film onto a concave spherical surface of a substrate. Because of a tendency of the disk to break during mounting to the curvature, a number of platelets may be bonded to the surface, for example in a monochrometer used in a PHI model 5600 instrument sold by Perkin-Elmer. Bonding techniques include brazing, optical contacting, epoxy and the like. The platelets are cut sequentially from the end of a single crystal rod of quartz.

A second approach to reduced area analysis has been to use an x-ray beam that floods the specimen surface, combined with a small-area objective lens for the photoelectrons, such as taught in U.S. Pat. No. Re. 33,275 (Wardell et al) for an electrostatic objective lens. Direct XPS imaging of a surface flooded with x-rays, using a type of magnetic lens variously known as an immersion lens, single pole piece lens or snorkel lens, as taught in U.S. Pat. Nos. 4,810,880 (Gerlach) and 4,810,879 (Walker).

Scanning for XPS may be effected by rastering the sample or the analyzer system mechanically, which is cumbersome. Scanning is also achieved by electronic deflection in the objective lens to receive electrons from off-axis, in a manner as described in an article "A Wide-angle Secondary Ion Probe for Organic Ion Imaging" by C. C. Grimm, R. T. Short, and P. J. Todd, J. Am Soc. Mass. Spectrum 1991, 2, 362–371. Scanning of the objective lens for generating photoelectron images is disclosed in the aforementioned U.S. patent No. 4,752,685, and in an article "AXIS: An Imaging X-Ray Photoelectron Spectrometer" by I. W. Drummond, F. J. Street, L. P. Ogden, and D. J. Surman, SCANNING 13, 149–163 (March–April 1991).

A higher resolution type of x-ray microscope utilizes zone plates and mirror techniques. This requires a very intense source of x-rays such as from a synchrotron, and so is not practical for general use.

SUMMARY OF THE INVENTION

An object of the present invention is to provide an improved instrument for chemometric mapping across a surface area by x-ray photoelectron analysis. A specific object for such an instrument is to provide for compensation of shifts in electron energy across such a surface area. Another object is to provide improved mapping as well as summed-area information for insulators by x-ray photoelectron analysis. A further object is to provide an electron energy analyzer system to serve as a high performance secondary electron detector for imaging. Yet another object is to provide a high performance chemometric analyzer.

These and other objects are achieved, at least in part, by a scanning x-ray instrument for analysis of a specimen surface, wherein the instrument includes an electron gun for producing a focused electron beam, and an anode with an anode surface disposed to receive the focused electron beam so as to generate x-rays from an anode spot on the anode surface. The electron beam is rastered over the anode surface, thereby scanning the anode spot over the anode surface. The x-rays from the scanning anode spot are focused, advantageously by a concave Bragg crystal monochromator, in an energy band of x-rays as an x-ray spot on a pixel area scanning correspondingly over the specimen surface. Photoelectrons are thereby emitted from the scanning pixel area with electron energies characteristic of chemical species at the pixel area. An analyzer means is receptive of photoelectrons from the scanning pixel area for analyzing the electron energies. The analyzer means includes a detector receptive of the photoelectrons for generating corresponding photoelectron signals. A processing means receptive of the signals is cooperative with the rastering means and the analyzer means for generating specimen information representative of the electron energies and thereby chemical species of the specimen surface.

In one aspect of the invention, the x-rays and thereby the photoelectrons have a natural energy shift across the specimen surface. A compensating means is associated with the analyzer means for compensating for the shift. Advantageously the analyzer means comprises a hemispherical electrostatic deflector to deflect photoelectrons for detection according to a selected pass energy. In a preferable embodiment, the analyzer further comprises a lens means receptive of electrons from the specimen surface for transitting the electrons to the analyzer means in a pass energy range. A selected voltage is applied between the lens means and the deflector, the selected voltage being determinative of the pass energy range. The compensating means then coordinates the voltage means with the rastering means to correspondingly modulate the selected voltage to compensate for the shift.

In further aspects of the invention, the above-described scanning x-ray instrument may be utilized for analysis of an electrically insulating specimen surface. In one such aspect, the processing means sums the signals from across the selected area to generate information representative of chemical species summed over the selected area of the specimen surface. A blocking means blocks information of peripheral areas of the selected area from the summing. The rastering should be sufficiently rapid so that charge potential on the pixel area scanning across the specimen surface does not change significantly during x-ray spot dwell time.

Objects are also achieved with an instrument for analysis of a specimen surface, wherein the instrument includes beam means for directing an energy beam to a pixel area on a specimen surface so as to emit electrons from the specimen surface. The energy beam may be a focused electron beam or a focused x-ray beam such as described above. The emitted electrons are in ranges of lower energy, such as 1–10 eV, and higher energy, such as 300–1500 eV. The lower energy range is representative of features of the specimen surface, and the higher energy range is characteristic of chemical species in the specimen surface. The beam is rastered over the specimen surface, thereby scanning the pixel area of emitting electrons over the surface. An analyzer means is receptive of electrons in a pass energy range generally between 3 eV and 300 eV, for producing signals representative of said electrons.

A lens means is receptive of electrons from the specimen surface for selectively transitting electrons from the specimen surface to the analyzer means, the lens means modifying energies of the transitted electrons into the pass energy range. A control means selectively controls the lens means to operate in a first mode or a second mode, the first mode being to modify the electron energies from the lower energy range into the pass energy range, and the second mode being to modify the electron energies from the higher energy range into the pass energy range. A display means is receptive of the analyzer signals cooperatively with the rastering means for displaying information associated with the pixel area scanning across the specimen surface. In response to the control means, the information provides an imaging of the specimen surface for the first mode, or a mapping of chemical species in the specimen surface for the second mode.

In a preferred embodiment, the lens means comprises a first electrode receptive of electrons from the specimen surface for transitting the electrons, a second electrode spaced coaxially from the first electrode for further transitting the electrons. More preferably, the first electrode and the second electrode are each in the form of a grid that is concave toward the specimen surface. An electron focusing means extends coaxially from the second electrode toward the analyzer for focusing to the analyzer said electrons with energies modified into the pass energy range. The control means comprises means for applying a first potential to the first electrode, and a second potential to the second electrode. The second potential is negative with respect to the first potential, and the first potential selectively is positive with respect to the specimen for the first mode, and the same potential as the specimen for the second mode.

In the case of the specimen surface being electrically insulating, the instrument preferably further comprises flood means for flooding the specimen surface with low energy electrons during periodic intervals so as to neutralize loss of photoelectrons from the specimen surface. The analyzer signals are omitted from effecting the information during the periodic intervals for the first mode. In the embodiment of the dual mode lens, the first potential is made equal (or positive) with respect to the specimen during the periodic intervals for the first mode.

DETAILED DESCRIPTION OF THE INVENTION

Figure 1:
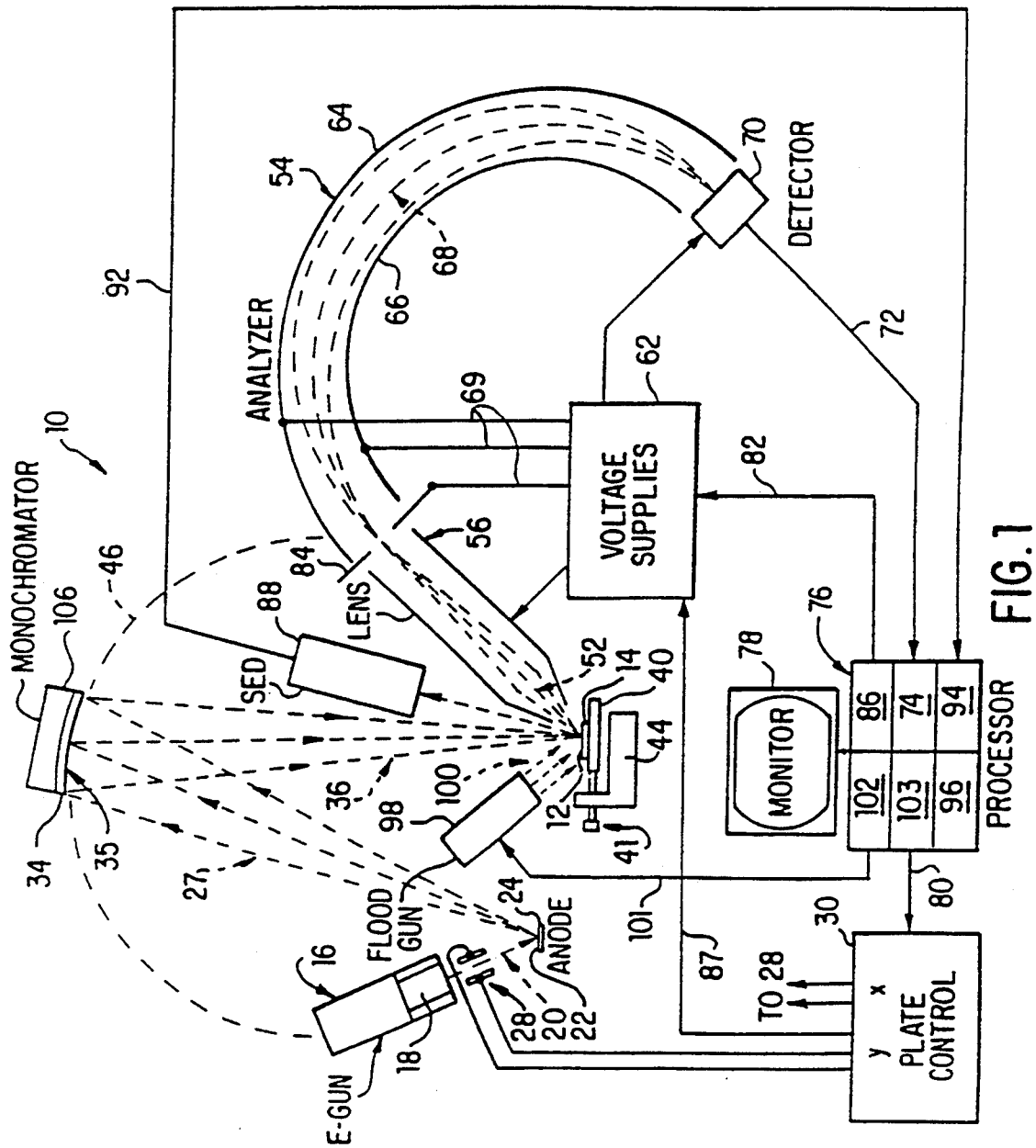
FIG. 1 is a schematic diagram of an instrument incorporating the invention.

An instrument 10 for analysis of a surface 12 of a sample specimen 14 is illustrated schematically in FIG. 1. An electron gun 16 has an appropriate electron lens system 18 for focusing an electron beam 20 onto the surface 22 of a target anode 24. The gun may be a conventional type, modified to optimize for higher power and larger beam size. The electron beam 20 should focus to a spot 26 (FIG. 3) on the anode surface, the spot being as small as practical, e.g. down to about 4 microns. This results in the generation of x-rays 27 from the anode, and in particular from the anode spot.

Figure 2:
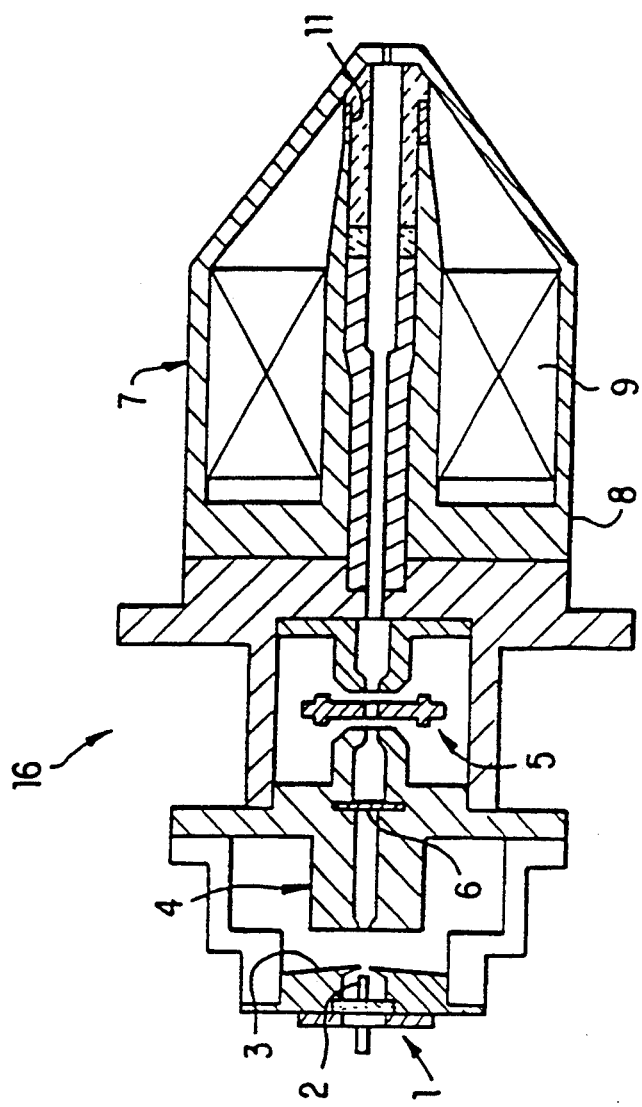
FIG. 2 is a longitudinal section of an electron gun used in the instrument of FIG. 1.

FIG. 2 illustrates a useful electron gun 16. At the rear is a cathode assembly 1 with a $LaB_6$ cathode 2, a wenwelt 3 and a gun anode 4. The mid portion includes an electrostatic condenser lens 5 with a condenser aperture 6. A magnetic objective lens 7 includes a polepiece 8 and a coil 9. Deflection of the beam is effected with an electrostatic deflector 11. The gun is operated at 10 to 20 KV over 1 to 60 watts with a selectable beam size of 4 to 250 microns.

The anode 24 may be formed of any metal such as aluminum that provides a desired x-ray emission energy band; ordinarily the band is substantially a line of small energy width. The anode should be at or near ground potential, and the gun cathode is operated at a negative voltage, for example −20 KV, with respect to the anode to effect generation of x-rays including the desired band of x-rays of predetermined energy. Advantageously the selected energy band is the aluminum K-alpha line at 1.4866 KeV.

Deflection plates 28 (one pair shown in FIG. 1) direct the electron beam 20 from the electron gun 16 to the anode spot 26 among an array of such spot locations 32 on the anode surface 22. Voltages from a deflection plate control 30, which is controlled by a processor 76 via line 80, are applied to the deflector plates arranged in both x and y axes to deflect the beam. The control 30 rasters the focused electron beam 20 across the surface of the anode, thereby scanning the anode spot across the anode surface, and x-rays 27 are emitted from the anode at the scanning anode spot. Raster speed is at least 0.5 microseconds per pixel, for example 1 to 10 microseconds.

A Bragg crystal monochromator 34, advantageously single-crystal quartz, is disposed to receive a portion of the x-rays 27 from the anode 24. The monochromator has a crystallographic orientation and a concave configuration 35 to select and focus a beam of x-rays 36 in the desired energy band, e.g. the K-alpha line, as an x-ray spot 38 on the specimen surface 12 to be analyzed. The x-ray spot on the specimen is an image of the anode spot 26. The specimen 14 rests on a stage 40 that may have orthogonal micrometer positioners 42 for manual or motorized positioning with respect to a support 44 in the instrument.

Although a Bragg crystal monochromator is preferred, other focussing means may be suitable. These include grazing incidence mirrors and synthetic multi-layer devices of alternating high and low density material (e.g. tungsten and carbon). In each case the reflector is curved in two dimensions to focus the diffracted x-rays onto the specimen.

A suitable arrangement is based on the conventional Rowland circle 46, in which the anode surface 22, the crystal 34 and the sample surface 12 are substantially on the circle, for example as taught in the aforementioned U.S. Pat. No. 3,772,522. In the plane of the drawing, the crystal has a radius of curvature equal to the diameter of the Rowland circle. For point focussing, the radius of curvature in the plane orthoganal to the drawing is $(2R*cos^2 B)$ where R is the circle radius and B is the Bragg angle. For example, the respective radii are 50 and 48 cm for quartz cut in a (100) plane, aluminum K-alpha x-rays and a Rowland circle radius of 25 cm. (The (100) plane is also known as a y-axis plane or a "zero degree y cut".) These are curvatures of the crystal lattice, not ground-in curvatures on the surface. For optimal point-to-point focussing, the crystals should be ellipsoidal.

Figure 3:
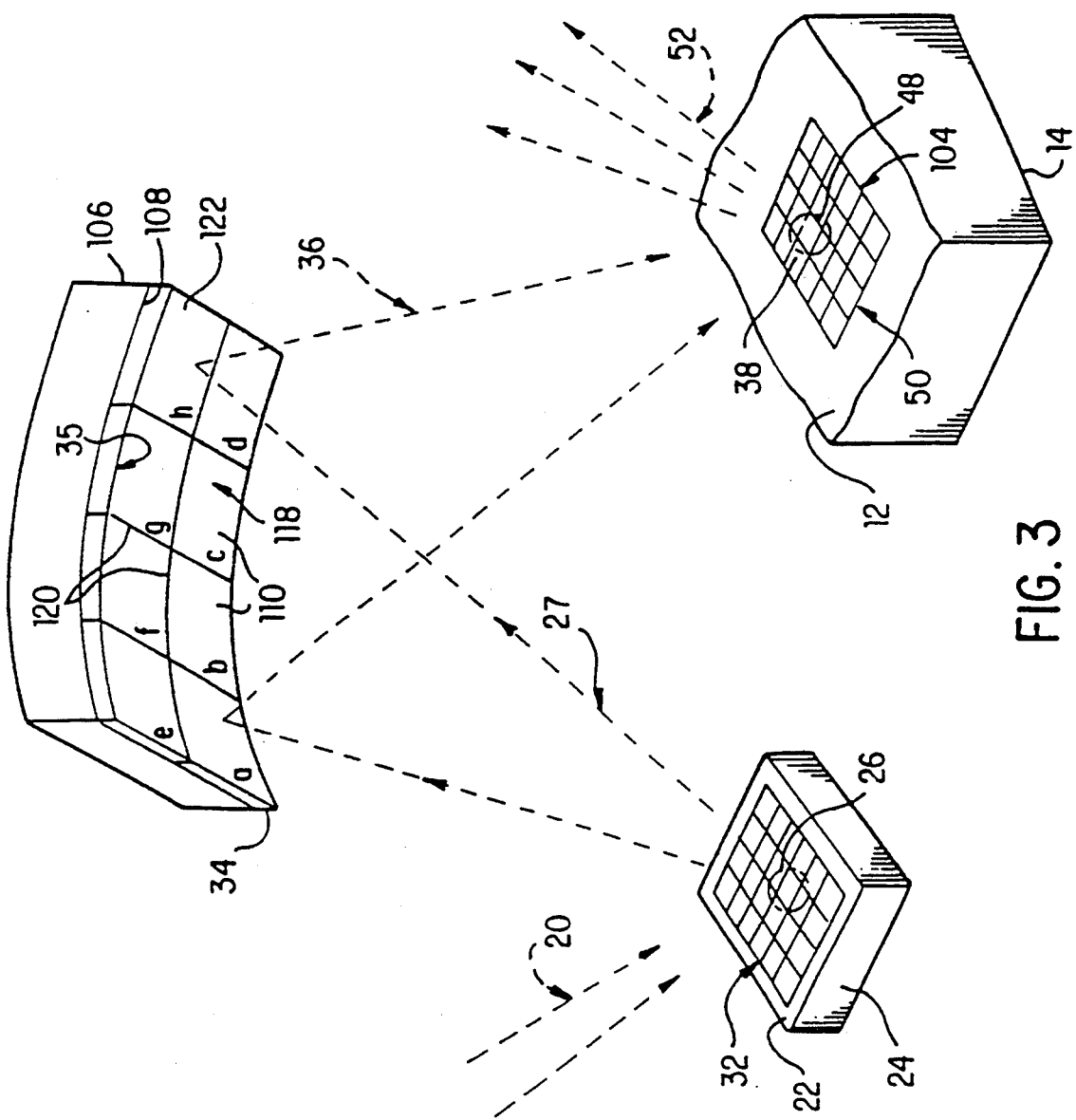
FIG. 3 is a detail in perspective of an anode, a specimen and a monochromator in the instrument of FIG. 1.

The focusing of the energy band of x-rays 36 effects the x-ray spot 38 on a selected pixel area 48 of the specimen surface 12 (FIG. 3). This pixel area, which coincides with the x-ray spot, is an x-ray image of the anode spot 26. Pixel 48 is in an array of such pixel locations 50 corresponding to the array of anode spots 32. The selected pixel area thereby corresponds to the selected anode spot, the location of which is determined by selection of voltages on the deflection plates 28 for the electron beam 20. Thus the position of the pixel area is effectively selected via these deflection voltages. With rastering, the anode spot location is continually changing, being each sequential spot location in the array on the anode surface. The rastering of the focused beam over the array of anode spots is such that the x-ray spot is correspondingly rastered over the array of pixel locations 50 covering a desired surface area of the specimen surface.

The x-rays 36 cause photoelectrons 52 to be emitted from the active, scanning pixel area 48 of the specimen. The electron kinetic energies generally include a low energy peak in the range of up to 10 ev, usually about 2 to 5 ev, plus higher kinetic energy peaks or lines characteristic of chemical species (viz. chemical elements and/or their electron bondings) in the selected pixel area. With the rastering, characteristic higher energy photoelectrons vary with chemistry across the specimen surface, and the low energy electrons (commonly known as "secondary electrons") vary with topography as well. The photoelectron spectrum provides information on the surface at a selected pixel area or across the rastered array of areas. There also may be Auger electrons which, for the present purpose, are included in the term "photoelectrons" as they are caused by the x-rays.

High scanning speeds may be desirable to allow increased power and uniform charging. Scanning speed may be between zero (for a selected spot) and 100 m/sec, for example 10 m/sec. Time per pixel area may be about one microsecond, with the mapping and imaging being built up from thousands of frames.

In one embodiment of the invention (FIG. 1) an electron energy analyzer 54 receives a portion of the photoelectrons 52. The analyzer may be a known or desired type, generally either magnetic or electrostatic, which deflects the photoelectrons in a predetermined path 68 according to electron energy and thence to a detector 70. A selected control signal (either a current or a voltage difference), is applied to the analyzer system to establish the amount of deflection, so that the signal level is representative of selected energy of photoelectrons deflected in the predetermined path. In a magnetic analyzer such as a magnetic prism, a current signal through the magnet coils is appropriately selected. In an electrostatic analyzer a deflecting voltage signal is selected.

The electrostatic energy analyzer may be a radial cylindrical type described in the aforementioned U.S. Pat. No. 4,048,498. Preferably, as shown in FIG. 1, the analyzer 54 is a hemispherical type as described in the aforementioned U.S. Pat. No. 3,766,381. The analyzing means also includes a lens system 56 such as an electrostatic lens for focusing the input to the analyzer. The lens usually combines objective and energy modifying functions to collect photoelectrons emitted from the effective pixel area and direct them into the analyzer in a desired pass energy range.

Figure 4:
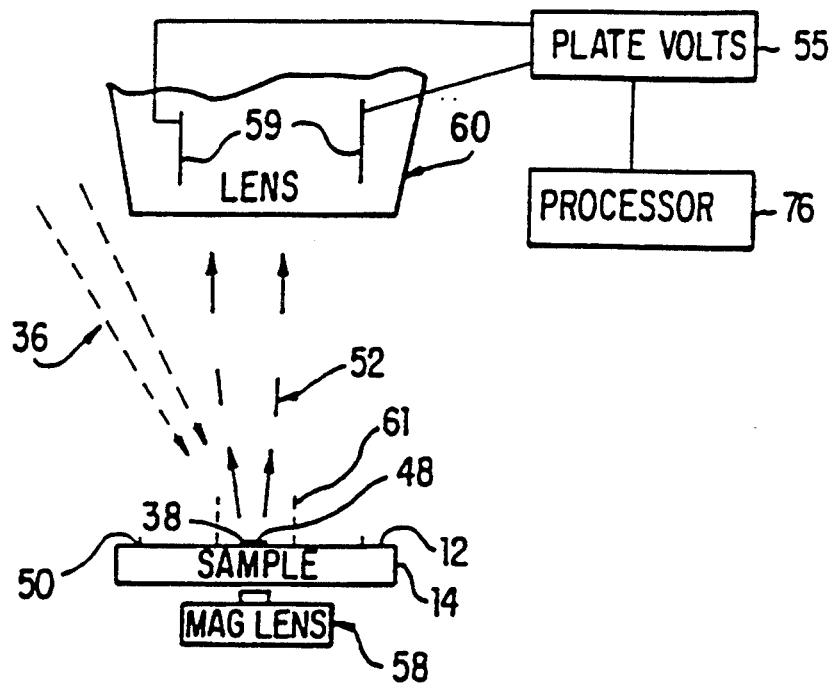
FIG. 4 is an elevation of an alternative embodiment for a magnetic lens for the instrument of FIG. 1.

The electrostatic lens 56 may be conventional, for example a PHI Omnifocus IV TM lens of Perkin-Elmer. The lens may include pairs of orthogonal deflection plates 59 with applied voltages from a source 55 (FIG. 4). The voltages on the plates are selected, varied or oscillated via the processor 76 in cooperative synchronization with positioning or rastering of the primary electron beam 20, under control of the processor, to centralize off-axis photoelectrons so that a substantial portion of the electrons reach the slit of stop 84 and enter into the analyzer 54.

An alternative for the objective lens function is a magnetic lens 58 (FIG. 4), advantageously of a type variously known as an immersion lens, a single pole piece lens or a snorkel lens as described in the aforementioned U.S. Pat. No. 4,810,880. This objective lens is situated below the specimen so that the magnetic field of the lens collects a substantial portion of the emitted photoelectrons 52 from the sample surface. To achieve this, the sample is placed proximate the immersion lens, the sample being interposed between the immersion lens and a separate electrostatic lens 60; in this case lenses 58 and 60 form the lens system 56 (FIG. 1). More generally, the sample is located between the immersion lens and the analyzer. If the magnetic lens has a collection field (illustratively delineated by broken lines 61) smaller than the rastered area, off-center emissions may be centered by deflector plates 59. Particularly good collection efficiency and sensitivity are attained with such a system.

Returning to FIG. 1, with a selected voltage from a voltage source 62 applied via lines 69 across the hemispheres 64,66 of the analyzer, electrons of selected energy travel in a range of trajectories 68 so as to exit the analyzer into the detector 70. The latter may be a conventional multichannel detector, for example having 16 channels for detecting a range of electron energies passed by the analyzer in slightly different trajectories. A further lens (not shown) may be placed between the analyzer and the detector, if desired or required for certain types of detectors.

Signals from the detector 70, corresponding to the number and energy of electrons detected, are carried on a line or lines 72 (via an appropriate amplifier, not shown) to an analyzing portion 74 of the processing unit 76 which combines control electronics and computer processing, such as with a Hewlett Packard Model 425e computer. The processing converts the spectral data to information on chemical species that are present at the particular specimen pixel area 48 (FIG. 3). The information is stored, displayed on a monitor 78, and/or printed out in the form of images, tables and/or graphs. By cooperating the display means (which herein includes the processor) with the electron beam directing means 28,30, via line 80 from the processor to the controller 30, a mapping of the chemical species in the selected or scanned surface area is effected and displayed. The mapping provides specimen surface information corresponding to the rastered array of pixel areas on the specimen surface.

As indicated above, voltages for the analyzer system including hemispheres 64,66, entrance aperture stop 84, input lens 56 and detector 70, are provided by the voltage supplies 62 under control of the processor 76 via control lines 82. The voltages may be set to detect a particular photoelectron line or may be ramped to produce a wider range spectrum covering several chemical species. For full area spectral analysis, rastered data from the whole scanned area of the specimen surface are summed to obtain an average spectral analysis of the entire rastered area of an insulator.

A complication arises because scanning the electron beam in the dispersive direction (in the plane of FIG. 1), for example when using a Bragg crystal monochromator 34, causes a small shift in the x-ray energy and hence the kinetic energy of the photoelectron lines across the specimen surface. Moreover, the scanning range may be limited by the width of the x-ray line, e.g. aluminum K-alpha, and the intensity will be modulated by the line shape. Means for compensating for such shifts may be effected in several ways.

One way is to raster (oscillate) the sample instead of the electron beam. In another way the electron beam is rastered over the anode and the data is acquired with an energy analyzer (such as the spherical analyzer of FIG. 1) with an energy window wide enough to capture the shifting spectral features; software is designed to shift the spectra to a constant energy. In yet another way the geometry of the analyzer is such that the dispersion of the monochromator is compensated, as taught in the aforementioned U.S. Pat. No. 3,567,926. Or the orientation of the monochromator may be synchronously modulated so that the x-ray energy stays constant and the intensity is always maximized at the x-ray line peak.

Another way of compensating is to have a section 86 of the processor 76 vary the energy control signal from the voltage controller 62 to the analyzer 64 synchronously with the scanning of the electron beam. For example with an electrostatic analyzer, the voltages on the analyzer hemispheres 64,66 and the entrance stop 84 are all modulated synchronously with the scanning of the electron beam in such a way that acquisition is essentially constant in energy. This may be effected with software (or firmware) in the processor to effect a sawtooth modulation. The software is readily assembled from theoretical or experimental determinations of voltage changes necessary to maintain constant energy of a selected peak as the beam 20 is scanned over the anode 24. Thus the processor 76 may be programmed to coordinate the voltage supply 62 with the rastering means 28,30 to correspondingly vary the voltage (or current) signal on lines 69 to the analyzer components to compensate for the variation.

A simple and preferred way of coordinating the analyzer voltage to compensate is to tap a portion of the raster voltage from the deflector plates 28. Such portion is added via lines 87 to modulate the voltages on lines 69 to the analyzer hemispheres 64,68 and stop 84. The modulation amplitude is selected empirically to optimize compensation.

In another embodiment of the invention the instrument 10 includes a second detector 88 that is receptive of photoelectrons 90 directly from the specimen, specifically the low energy "secondary" elections of about up to 10 ev, without filtering by an analyzer. This detector then generates corresponding photoelectron signals. A further portion 94 of the processor 76 receives these signals via line 92 and is cooperative with the rastering means 28,30 to produce a secondary electron image of the surface and display it on the monitor 78. Like a monochrome photograph, the information content is mostly topographical.

The second detector 88, denoted herein as a secondary electron detector (SED) is of the conventional type ordinarily used for a scanning electron microscope (SEM). A suitable detector is a Perkin-Elmer Model 04-202 detector, with an appropriate amplifier and (if necessary) an analog-digital converter. The resulting secondary electron image is quite similar to that of an SEM operation, except that the detected electrons are generated by x-rays as described herein.

In an alternative embodiment for secondary electron imaging, the second detector 88 shown in FIG. 1 is omitted and a modified form of the lens system 56 is utilized. This embodiment is useful for instruments with rastered incident beams of electrons as well as rastered x-rays on the specimen surface. The modified lens is particularly suitable with a hemispherical electrostatic analyzer.

Figure 6:
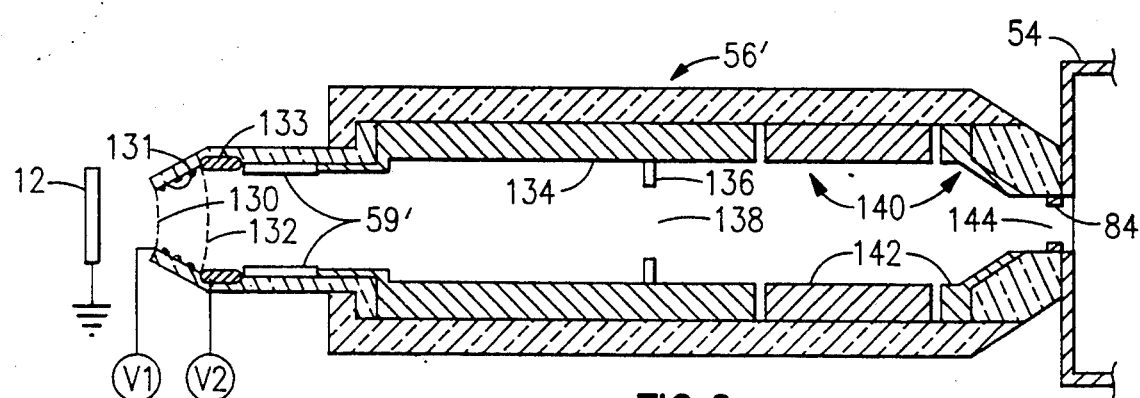
FIG. 6 is a schematic section of a lens component of the instrument of FIG. 1 wherein an imaging detector is omitted.

Basically the form and operation of the modified lens system 56' (FIG. 6) are based on recognition of three kinetic energy ranges for electrons: A lower energy range represents the secondary electrons emitted from the surface, typically up to 10 eV. These electrons are detected ordinarily by the omitted detector 88 for imaging of topographical and qualitative compositional features of the specimen surface. A higher energy range (typically 300–1500 eV) represents Auger electrons or photoelectrons that are emitted from the atomic shells and, therefore, are representative of chemical species in the specimen surface. Thirdly, the analyzer operates to detect electrons entering from the lens at a selected pass energy range in which the specific analyzer is operational. The pass energy is generally between the higher and lower energy ranges, typically between 3 eV and 300 eV with a pass energy range of 10% to 15% depending, conventionally, on a chosen tradeoff between high resolution (low pass energy) and high sensitivity (high pass energy). One function of either a conventional lens and the modified lens 56' is to adjust the higher energy electrons into the pass energy range selected for the analyzer.

The modified lens system 56' is operated selectively in a first mode or a second mode, so as to allow use of the analyzer 54 for imaging as an alternative to its normal function for detecting chemical species. In the first mode the electron energies in the lower energy range are changed to the pass energy for the imaging function of the analyzer. In the second mode the electron energies are changed from the higher energy range to the pass energy range for spectroscopic analysis of chemical species. The modes are selected by application of voltages to the lens from a control means which, in the present example, comprises the voltage supplies 62 and the voltage control section 86 of the processor 76. In practice, mode selection can shift between an acceleration of 20 times input electron velocity for imaging, and a retardation of up to 500 times for spectroscopy.

In the imaging mode, low energy secondary electrons are accelerated to a pass energy typically about 100 eV so that the entire 0–10 eV window is captured by the detector. In this mode, a positive potential is applied to the first grid to efficiently extract secondary electrons from the specimen. In the spectroscopy mode, electrons are retarded from higher energies to the selected pass energy for analysis of chemical species. In this mode, the first grid should be grounded with the specimen to keep the specimen field-free.

The lens 56' (FIG. 6) includes a first electrode 130 that is a ring, or preferably (as shown) a grid formed, for example, of 0.03 mm diameter conductors on 0.3 mm centers. The grid should be concave toward the specimen. A second, larger electrode 132, also preferably a grid, has a configuration similar to the first, and is spaced from the first in the direction of the analyzer. The grid curvatures are conveniently determined by standard, commercially available computer programming for electron optics to empirically ascertain optimum electron trajectories. Ideally the grids are axial sections of confocal ellipsoids. However, spherical approximations have been found to perform satisfactorily. A set of three intermediate electrode rings are spaced between the grids, which are set at progressive voltages intermediate to those of the grids.

At least one additional electrode follows the second grid coaxially therewith for further passing the electrons to the analyzer. In the present example, a ring electrode 133, a set of segmented electrodes 59' and a cylindrical electrode 134 extend tandemly from the second grid coaxially in the direction of electron flow toward the analyzer. Except for electrodes 59', these are is held at the same potential as the second grid, and the cylindrical electrode advantageously contains an aperture plate 136 with a central aperture 138. The electrodes 59' are optionally segmented in quarters and are nominally held at the same potential as the second grid but, if necessary, may be additionally biased orthoganally in the same manner and for the same purpose as the deflection electrodes 59 (FIG. 4), i.e. to adjust electron trajectories from off-axial as required. If such correction is not necessary, the segmented electrodes may be replaced by a cylinder.

The aperture 138 preferably is located cooperatively with selection of grid configurations and applied voltages so that the transitting electrons are deflected to cross over at the aperture. The cylinder 134 is followed by a conventional electron focusing lens system 140, such as a series of tandem cylindrical and conical electrodes 142 which adjust the energy of the electrons and focus them on an entrance aperture 144 to the analyzer. Other conventional or desired configurations for the lens portion 140 may be utilized.

For the usual spectroscopy function of the analyzer, which utilizes the second mode for the lens 56', the first grid 130 is at the same potential as the specimen 14 (which usually is grounded) so that the specimen is field-free. A voltage potential V2 on the second grid is a negative retarding potential (relative to the specimen), typically 90% of the initial energy. The field between the grids also acts as a lens to focus the electrons at the central aperture 138. The electrons are then focused into the analyzer where, by selection of the various lens voltages, they arrive in the ordinary pass energy range. The voltages on the analyzer are selected in the ordinary manner to detect specific energies correlated to chemical species for the specimen.

In the first mode, for imaging, a positive voltage V1 on the first grid (relative to the specimen) accelerates the low energy electrons from the specimen. Voltage V2 on the second grid is negative with respect to the first grid to retard and focus the electrons with the net energy being high enough to transport the electrons through. The analyzer voltages for the pass energy range on the hemispheres 64,66 (FIG. 1) are set for the analyzer to pass these electrons, and the voltages V1 and V2 are set to maximize the imaging signal. For example, V1 is +300 volts and V2 is +150 volts for this mode.

Figure 7:
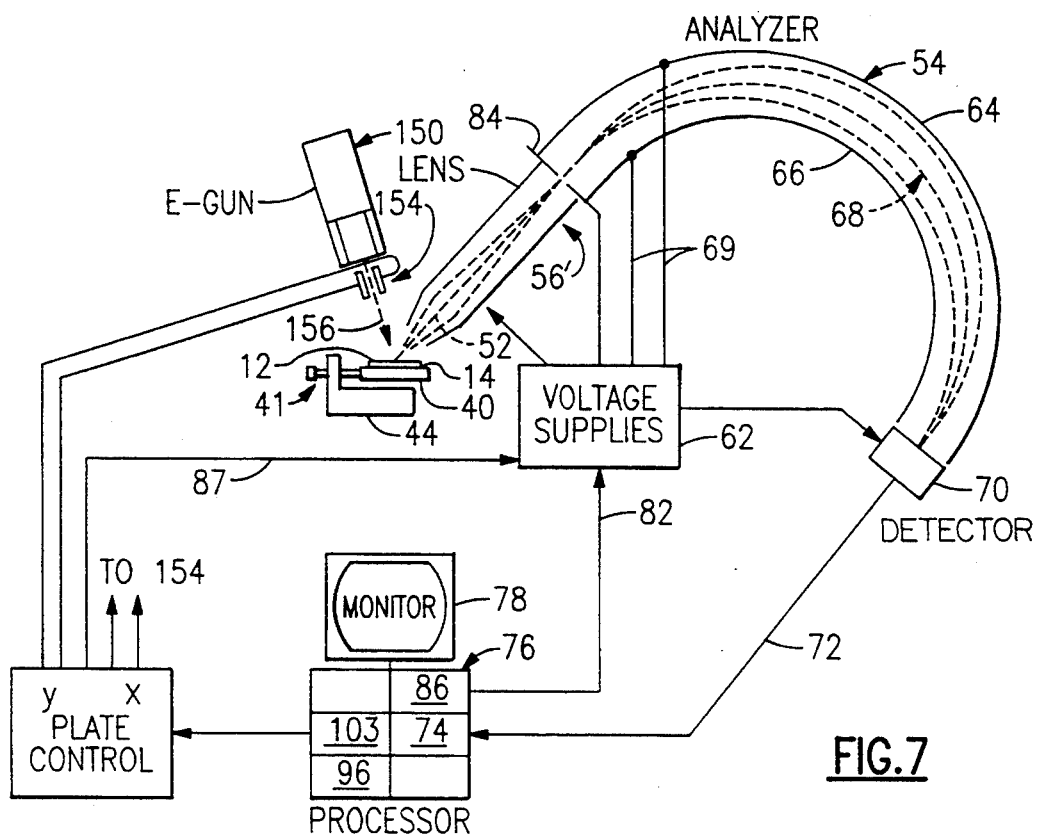
FIG. 7 is a schematic diagram of an alternative instrument incorporating the lens component of FIG. 6.

Performance of the analyzer with lens 56' in the imaging mode is generally significantly better than that of an ordinary scanning electron detector (SED), viz. detector 88 in FIG. 1. The provision for dual functioning of the analyzer is particularly useful with a scanning x-ray system for inducing photoelectrons as disclosed with respect to FIG. 1. The embodiment also is useful with a scanning Auger microprobe of the type disclosed in the aforementioned U.S. Pat. No. 4,048,498, and illustrated in FIG. 7. For Auger spectroscopy, an electron gun 150 with deflection plates 154 is substituted for the x-ray scanning system, and all other relevant components are essentially the same as in FIG. 1 (omitting SED 88, flood gun 98 and associated processor components); these are given the same numeral designations, and component descriptions are not repeated here. The electron gun may be the same type as gun 16, to direct a focussed electron beam 156 to the specimen surface 12.

The secondary electron image with the first mode is useful particularly for locating an area on the specimen surface to be analyzed for chemical species by the energy analyzing embodiment. For example the image may be viewed on the monitor 78 while the specimen 14 is moved with the stage 40 (FIG. 1). Since the image and analysis modes are effected from the same focus of x-rays, the locations are substantially identical for both.

The scanning x-ray embodiment for topographical imaging or chemical mapping, or for summing of chemical information over the surface, is advantageous for specimens of electrically insulating material because the primary beam is neutral. Photoemission will cause the sample to charge positively and impede further emission, but this positive charging is readily neutralized by flooding the specimen with a with low energy electrons 100 (generally 1–10 eV and 0.1–10 $\mu$A) from a flood gun 98 such as a Perkin-Elmer model 04-090 electron gun or the like. The low energy electrons will not be detected through an analyzer for chemical mapping.

In rastering an insulator for an image from low energy secondary electrons, the instrument preferably further comprises pause means 102 in the programming for periodically pausing the imaging. The flood gun 98 is then operated during each pause under direction of the processor portion 102 via line 101 to irradiate the specimen surface 12 with a low level pulse (generally 0.1 to 10 microamperes) of electrons 100 at about one microampere so as to neutralize loss of photoelectrons from the surface during rastering. Pausing with the pulses is necessary because detection of the low-energy flood electrons would add noise to the image. The pulses and simultaneous pauses may, for example, be of 10 millisecond duration at 1 second intervals. If the mode lens 56' is used with the analyzer for imaging, the first grid 130 should be pulsed simultaneously to equal (or positive) potential with respect to the specimen (generally ground) so that the flood electrons can reach the sample instead of being extracted into the lens. The imaging detector for this aspect alternatively may comprise an ordinary SED 88.

For electrically insulating specimens, the rastering should be carried out rapidly for an insulator so as to minimize differential charging across the surface with a time dependence that can result in line broadening for the electron energies. Scanning should be rapid enough so that the potential on the scanning pixel does not change significantly during dwell time at each pixel location. The charging potential should be held to less than about 0.1 volt. With a typical capacitance of $3 \times 10^{-17}$ coulombs/volt in a 10 $\mu$m pixel area, and a typical photocurrent of $1 \times 10^{-12}$ amperes, there will be charging of 0.03 volts at 1 microsecond per pixel area; therefore, scanning rates faster than about 3 microseconds per pixel are required to keep charging less than 0.1 volt.

Differential charging effects may occur at the edges of a rastered area of an insulator where full-area analysis is being performed. To account for this, the processor may include means 103 such as software for blocking ("gating") data from peripheral pixels areas 104 (FIG. 3) of the array from the spectral data. The width of the gating may be the outer one or two or more pixel widths, a selected width being readily determined empirically to sufficiently reduce the differential charging effects. The combination of edge gating and rapid scanning provides excellent energy resolution on insulators.

For clarity the several functional portions of the processor 76 are shown separately in FIG. 1. However such portions actually may include a commonality of components and various sections of a computer program. Any computer programs mentioned or implied herein are readily prepared in a conventional language such as "C" generally available from the supplier of the computer used. Some portions of the programming may be embedded in PROM chips as firmware.

Analysis is advantageously effected with a very small anode spot 26 combined with a precision monochromator 34 to focus a similarly small spot 38 of the selected energy band of x-rays on the specimen. As indicated above, the monochromator crystal is oriented crystallographically to effect the selected x-ray band, and is curved for the focusing. For example a quartz crystal will be oriented (prior to curvature) in a (100) plane. The monochromator is advantageously mounted on a base member 106 having a polished face 108 with the desired concave curvature, as a thin crystal 34 bonded to the face so as to assume the curvature. The base plate should be of the same or similar material as the crystal to match thermal expansion coefficients. A quartz base or a glass with similar expansion coefficient is a suitable base for quartz crystal.

To facilitate construction the monochromator crystal 34 advantageously comprises a plurality of crystal platelets 110 having a uniform thickness. The platelets are formed of common (same) material, lattice structure, and crystalline orientation with respect to a polished surface of the platelets bonded to the base member. The crystal platelets are bonded to the face 108 juxtaposed like tiles in crystalline alignment so as to assume the concave curvature. The bonding may be by conventional means but should introduce as little imperfection to the interface as possible.

Figure 5:
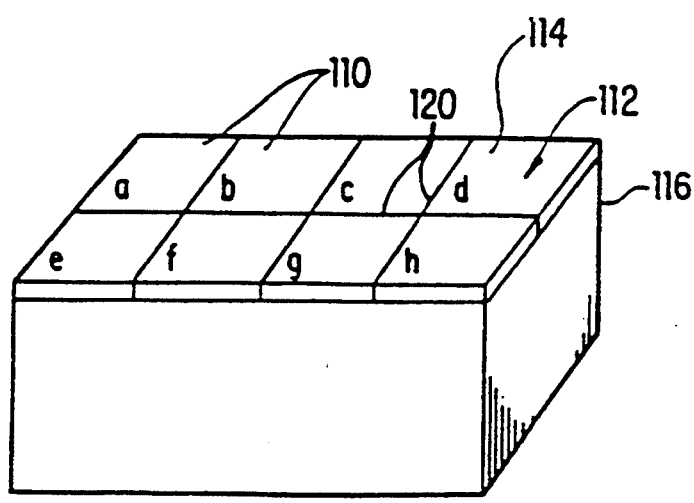
FIG. 5 is a perspective of a crystal member used for forming the monochromator of FIG. 3.

According to a preferred embodiment (FIG. 5) the platelets 110 are produced by delineating an initial array 112 of juxtaposed sections from a planar surface 114 of a single crystal member 116 and cutting the delineated sections from the member. Alternatively the single crystal may be cut initially to the desired thickness of the platelets, before delineating and cutting the platelets. Polished sides of the platelets are then bonded to the polished face 108 in a positioned array 118 (FIG. 3) with crystallographic alignment identical to that of the initial array 112. The initial and positioned arrays are illustrated by the lettering a through h respectively in FIGS. 5 and 3. This origination of platelets ensures that the platelets are formed of common material, lattice structure and crystalline orientation.

To produce a monochromator of high precision, the following procedure is advantageous: A 40 by 40 mm quartz crystal 5 to 10 mm thick is prepared with a large face oriented zero degrees to the y-axis. The crystal should be thick enough for rigidity during subsequent polishing and thinning but not so thick as to unduly encumber the subsequent thinning process. The crystal is examined interferometrically and rejected if twinned. The large face is lapped and polished optically flat, preferably within one-tenth wave per inch (0.04 wave/cm) at a wavelength of 632.8 nm. This polished face is x-rayed near the center and each corner to establish that the orientation at each point is exactly the same, and the mean is within one arc-minute of the y-axis. The platelets are contacted to an optically flat support member, e.g. within one-tenth wave per inch (0.04 wave/cm), retaining the same juxtaposition of relative locations (including rotation) with crystallographic alignment as in the original crystal. The platelets are thinned to a final predetermined thickness between 50 and 100 microns (uniform preferably within ±5 microns) and polished so the faces are parallel within one-tenth wave per inch (0.04 wave/cm) over the entire 40 by 40 mm. The platelets are removed from the support member and bonded to the polished face of the base member in the same relative locations (including rotation) as in the original crystal.

Numbers of platelets ranging from 2 to 16 in a total area of 40 by 40 mm may be suitable. Each side dimension is advantageously in the range of 10 to 20 mm. The sensitivity of the monochromator is substantially proportional to the solid angle of radiation intercepted as viewed from the anode, approximately according to the formula $A/D^2$ where A is crystal area and D is Rowland circle diameter. Larger solid angles improve sensitivity but introduce aberrations limiting both energy and spatial resolution. For the dimensions given herein, the solid angle is 0.04 steradians. Such a monochromator can provide an x-ray spot on the specimen that is substantially the same size as the electron beam on the anode, subject only to monochromator broadening of about 10 microns.

While the invention has been described above in detail with reference to specific embodiments, various changes and modifications which fall within the spirit of the invention and scope of the appended claims will become apparent to those skilled in this art. The invention is therefore only intended to be limited by the appended claims or their equivalents.

We claim:

1. An instrument for analysis of a specimen surface, comprising:

an electron gun for producing a focused electron beam;

an anode with an anode surface disposed to receive the focused electron beam so as to generate x-rays from an anode spot on the anode surface;

rastering means for rastering the focused electron beam over the anode surface, thereby scanning the anode spot over the anode surface;

focusing means receptive of at least a portion of the x-rays from the scanning anode spot for focusing an energy band of x-rays of predetermined energy as an x-ray spot on a pixel area scanning correspondingly over the specimen surface, such that photoelectrons are emitted from the scanning pixel area with electron energies characteristic of chemical species at the pixel area, wherein the x-rays and thereby the photoelectrons have a natural energy shift across the specimen surface;

analyzer means receptive of at least a portion of the photoelectrons from the scanning pixel area for analyzing the electron energies;

compensating means associated with the analyzer means for compensating for the shift; and processing means cooperative with the rastering means and the analyzer means for generating specimen information representative of the electron energies and thereby chemical species of the specimen surface.

2. The instrument of claim 1 wherein the processing means is cooperative with the rastering means and the analyzer means for displaying a mapping of the electron energies and thereby the chemical species across the specimen surface.

3. The instrument of claim 2 wherein the analyzer means comprises electrostatic deflector means to deflect at least a portion of the photoelectrons in a predetermined path for detection according to selected pass energy, and voltage means for applying to the deflector means a selected voltage determinative of the path and thereby the selected pass energy, and the compensating means comprises means for coordinating the voltage means with the rastering means to correspondingly modulate the selected voltage to compensate for the shift.

4. The instrument of claim 3 wherein the analyzer means comprises hemispherical electrostatic deflector means to deflect at least a portion of the photoelectrons for detection according to a predetermined pass energy, lens means receptive of photoelectrons from the specimen surface for transitting the photoelectrons from the specimen surface to the analyzer means in a selected energy range, and voltage means for applying between the lens means and the deflector means a selected voltage determinative of the selected energy range.

5. The instrument of claim 1 wherein the focusing means comprises a Bragg x-ray crystal monochromator having a concave curvature and being disposed cooperatively with the anode surface and the specimen surface so as to effect the x-ray spot in the predetermined energy band as an x-ray image of the anode spot.

6. An instrument for analysis of an electrically insulating specimen surface, comprising:
   an electron gun for producing a focused electron beam;
   an anode with an anode surface disposed to receive the focused electron beam so as to generate x-rays from an anode spot on the anode surface;
   rastering means for rastering the focused electron beam over the anode surface, thereby scanning the anode spot over the anode surface;
   focusing means receptive of at least a portion of the x-rays from the scanning anode spot for focusing an energy band of x-rays of predetermined energy as an x-ray spot on a pixel area scanning correspondingly over a selected area of the insulating specimen surface, such that photoelectron are emitted from the scanning pixel area with electron energies characteristic of chemical species at the pixel area;
   analyzer means receptive of at least a portion of the photoelectrons from the scanning of the pixel area for analyzing the electron energies and generating corresponding photoelectron signals;
   processing means for effecting a summing of the photoelectron signals across the selected area to generate information representative of chemical species summed over the selected area of the specimen surface; and
   blocking means for blocking information of peripheral areas of the selected area from the summing.

7. The instrument of claim 6 wherein the rastering is sufficiently rapid so that charge potential on the pixel area scanning across the insulating specimen surface does not change significantly during x-ray spot dwell time.

8. The instrument of claim 7 wherein the rastering is sufficiently rapid so that change in charge potential is less than 0.1 volt.

9. The instrument of claim 6 further comprising flood means for flooding the specimen surface with low energy electrons during periodic intervals so as to neutralize loss of photoelectrons from the specimen surface, wherein the processing means is receptive of the photoelectron signals and cooperative with the rastering means so as to produce data signals for effecting a presentation of specimen information representative of the specimen surface, wherein and during the periodic intervals the data signals are omitted from effecting the presentation during the periodic intervals.

10. The instrument of claim 6 wherein the focusing means comprises a Bragg x-ray crystal monochromator having a concave curvature and being disposed cooperatively with the anode surface and the specimen surface so as to effect the x-ray spot in the predetermined energy band as an x-ray image of the anode spot.

11. An instrument for analysis of a specimen surface, comprising:
   beam means for directing an energy beam to a pixel area on a specimen surface so as to emit electrons from the specimen surface, the electrons having ranges of lower energy and higher energy, the lower energy being representative of features of the specimen surface, and the higher energy being characteristic of chemical species in the specimen surface;
   rastering means for rastering the focused beam over the specimen surface, thereby scanning the pixel area of emitting electrons over the specimen surface;
   analyzer means receptive of electrons in a pass energy range for producing analyzer signals representative of said electrons;
   lens means receptive of electrons from the specimen surface for selectively transitting electrons to the analyzer means, the lens means modifying energies of the transitted electrons into the pass energy range;
   control means for selectively controlling the lens means to operate in a first mode or a second mode, wherein the first mode is to modify the electron energies from the lower energy range into the pass energy range, and the second mode being to modify the electron energies from the higher energy range into the pass energy range; and
   display means receptive of the analyzer signals and cooperative with the rastering means for displaying information representative of the specimen surface, whereby, in response to the control means, the information is representative of at least a portion of the features of the specimen surface for the first mode, or is characteristic of at least a portion of the chemical species in the specimen surface for the second mode.

12. The instrument of claim 11 wherein the beam means comprises an electron gun for directing a focused electron beam to the specimen surface so as to emit electrons from the specimen surface, and rastering means for rastering the electron beam over the specimen surface, the electron beam constituting the energy beam.

13. The instrument of claim 11 wherein the beam means comprises an electron gun for producing a focused electron beam, an anode with an anode surface disposed to receive the focused electron beam so as to generate x-rays from an anode spot on the anode surface, rastering means for rastering the focused beam over the anode surface to thereby scan the anode spot over the anode surface, and focusing means receptive of at least a portion of the x-rays from the scanning anode spot for focusing an energy band of x-rays of predetermined energy as an x-ray spot on a pixel area scanning correspondingly over the specimen surface, the focused x-rays constituting the energy beam such that photoelectrons are emitted from the scanning pixel area, the photoelectrons having energies in the lower and higher energy ranges.

14. The instrument of claim 13 wherein the display means is cooperative with the rastering means for displaying a scanning photoelectron image for the first mode, and a mapping of chemical species for the second mode.

15. The instrument of claim 11 wherein the pass energy range is generally between the lower energy range and the higher energy range, the lens means comprises a first electrode receptive of electrons from the specimen surface for transitting said electrons, a second electrode spaced coaxially from the first electrode for further transitting said electrons, and an electron focusing means extending coaxially from the second electrode toward the analyzer for focusing to the analyzer said electrons with energies modified into the pass energy range, and the control means comprises means for applying a first potential to the first electrode and a second potential to the second electrode, the second potential being negative with respect to the first potential, and the first potential selectively being a positive potential with respect to the specimen for the first mode, and the same potential as the specimen for the second mode.

16. The instrument of claim 15 wherein the first electrode and the second electrode are each in the form of a grid that is concave with a center of curvature substantially at the specimen surface.

17. The instrument of claim 16 wherein the electron focusing means comprises a cylindrical electrode extending from the second electrode coaxially from the second electrode at the same potential thereof, an aperture wall with a central aperture in the cylindrical electrode distal from the second electrode, and a lens system disposed coaxially between the aperture wall and the analyzer, wherein the central aperture is located cooperatively with selection of relative potential between the first electrode and the second electrode for the transitted electrons to cross over at the aperture.

18. The instrument of claim 17 wherein the analyzer has an entrance aperture, and the lens system comprises a pair of tandem cylindrical electrodes with potentials applied thereto so as to focus the electrons at the entrance slit.

19. The instrument of claim 16 wherein the analyzer means comprises an electrostatic hemispherical analyzer.

20. The instrument of claim 19 wherein the beam means comprises an electron gun for directing a focused electron beam to the specimen surface so as to emit electrons from the specimen surface, and rastering means for rastering the electron beam over the specimen surface, the electron beam constituting the energy beam.

21. The instrument of claim 19 wherein the beam means comprises an electron gun for producing a focused electron beam, an anode with an anode surface disposed to receive the focused electron beam so as to generate x-rays from an anode spot on the anode surface, rastering means for rastering the focused beam over the anode surface to thereby scan the anode spot over the anode surface, and focusing means receptive of at least a portion of the x-rays from the scanning anode spot for focusing an energy band of x-rays of predetermined energy as an x-ray spot on a pixel area scanning correspondingly over the specimen surface, the focused x-rays constituting the energy beam such that photoelectrons are emitted from the scanning pixel area, the photoelectrons having energies in the lower and higher energy ranges.

22. The instrument of claim 21 wherein the focusing means comprises a Bragg x-ray crystal monochromator having a concave curvature and being disposed cooperatively with the anode surface and the specimen surface so as to effect the x-ray spot in the predetermined energy band as an x-ray image of the anode spot.

23. The instrument of claim 15 wherein the specimen surface is electrically insulating, the instrument further comprises flood means for flooding the specimen surface with low energy electrons during periodic intervals so as to neutralize loss of photoelectrons from the specimen surface, the control means further comprises means for making the first potential equal or positive with respect to the specimen during the periodic intervals for the first mode, and the display means comprises means for omitting the analyzer signals from effecting the information during the periodic intervals for the first mode.

24. An instrument for analysis of an insulating specimen surface, comprising:
   an electron gun for producing a focused electron beam;
   an anode with an anode surface disposed to receive the focused electron beam so as to generate x-rays from an anode spot on the anode surface;
   rastering means for rastering the focused electron beam over the anode surface, thereby scanning the anode spot over the anode surface;
   focusing means receptive of at least a portion of the x-rays from the scanning anode spot for focusing an energy band of x-rays of predetermined energy as an x-ray spot on a pixel area scanning correspondingly over the specimen surface, such that photoelectrons are emitted characteristically from the scanning pixel area;
   detector means receptive of the photoelectrons for generating corresponding photoelectron signals;
   flood means for flooding the specimen surface with low energy electrons during periodic intervals so as to neutralize loss of photoelectrons from the specimen surface; and
   processing means receptive of the photoelectron signals and cooperative with the rastering means so as to effect an imaging of the specimen surface, wherein the photoelectron signals are omitted from the imaging during the periodic intervals.

* * * * *